US009169290B2

(12) United States Patent
O'Neil

(10) Patent No.: US 9,169,290 B2
(45) Date of Patent: Oct. 27, 2015

(54) PEPTIDES AND THEIR USE

(75) Inventor: Deborah O'Neil, Aberdeen (GB)

(73) Assignee: NovaBiotics Limited, Aberdeen (GB)

( * ) Notice: Subject to any disclaimer, the term of this patent is extended or adjusted under 35 U.S.C. 154(b) by 1076 days.

(21) Appl. No.: 12/525,523

(22) PCT Filed: Jan. 28, 2008

(86) PCT No.: PCT/GB2008/000283
§ 371 (c)(1),
(2), (4) Date: Mar. 2, 2010

(87) PCT Pub. No.: WO2008/093060
PCT Pub. Date: Aug. 7, 2008

(65) Prior Publication Data
US 2010/0184696 A1    Jul. 22, 2010

Related U.S. Application Data

(60) Provisional application No. 60/899,283, filed on Feb. 2, 2007.

(30) Foreign Application Priority Data

Feb. 2, 2007 (GB) .................................. 0702020.9

(51) Int. Cl.
*C07K 7/08* (2006.01)
*A61K 38/10* (2006.01)
*A61K 38/08* (2006.01)
*C07K 7/06* (2006.01)

(52) U.S. Cl.
CPC . *C07K 7/08* (2013.01); *A61K 38/08* (2013.01); *A61K 38/10* (2013.01); *C07K 7/06* (2013.01)

(58) Field of Classification Search
CPC .................................. C07K 7/08; A61K 38/10
See application file for complete search history.

(56) References Cited

U.S. PATENT DOCUMENTS

| 5,646,120 A * | 7/1997 | Sumner-Smith et al. ....... 514/3.8 |
| 2003/0054999 A1 * | 3/2003 | May et al. ........................ 514/15 |
| 2003/0083262 A1 * | 5/2003 | Hannig et al. ................... 514/14 |
| 2003/0162719 A1 * | 8/2003 | Rothbard et al. ............... 514/14 |
| 2004/0142892 A1 * | 7/2004 | Finn et al. ....................... 514/44 |
| 2004/0229801 A1 | 11/2004 | Kawabe et al. |
| 2006/0166881 A1 * | 7/2006 | Hotchkiss et al. .............. 514/12 |

FOREIGN PATENT DOCUMENTS

| EP | 0149254 A2 | 7/1985 |
| WO | 2004/050685 A2 | 6/2004 |
| WO | 2006/018652 A2 | 2/2006 |
| WO | WO 2006/018652 | * 2/2006 |
| WO | 2007/072037 A1 | 6/2007 |
| WO | 2008/093058 A2 | 8/2008 |
| WO | 2008/093059 A1 | 8/2008 |

OTHER PUBLICATIONS

Narasimhan et al., 2001, A Plant Defense Response Effector Induces Microbial Apoptosis, Molecular Cell, 8: 921-930.*
Buchanan-Davidson et al., 1960, Effect of Synthetic Polylysine on Fungi, Science, 132(3440): 1664-1666.*
Lindegren et al., 2002, Synthesis and Biodistribution of 211At-Labeled, Biotinylated, and Charge-Modified Poly-L-lysine: Evaluation for Use as an Effector Molecule in Pretargeted Intraperitoneal Tumor Therapy, Bioconjugate Chem., 13: 502-509.*
Pollock et al., 1984, Fungistatic and Fungicidal Activity of Human Parotid Salivary Histidine-Rich Polypeptides on Candida albicans, Infection and Immunity, 44(3): 702-707.*
Sedlak et al., 2007, Synthesis and characterization of a new pH-sensitive amphotericin B-poly(ethylene glycol)-b-poly(lysine) conjugate, Bioorganic & Medicinal Chemistry Letters, 17: 2554-2557.*
Chamilos et al., 2005, Update on antifungal drug resistance mechanisms of Aspergillus fumigatus, Drug Resistance Updates, 8: 344-358.*
Uritani et al., 1994, Polyamino acids that inhibit the interaction of yeast translational elongation factor-3 (EF-3) with ribosomes, J. Biochem., 115: 820-824.*
Jung et al., 2006, Biological activity of Tat (47-58) peptide on human pathogenic fungi, Biochemical and Biophysical Research Communications, 345: 222-228.*
Pollock, Jerry J. et al., "Fungistatic and Fungicidal Activity of Human Parotid Salivary Histidine-Rich Polypeptides on Candida albicans," Infection and Immunity, vol. 44, No. 3, pp. 702-707 (Jun. 1984).
Zhu, Jingsong et al., "Synthetic Histidine-Rich Peptides Inhibit Candida Species and Other Fungi In Vitro: Role of Endocytosis and Treatment Implications," Antimicrobial Agents and Chemotherapy, vol. 50, No. 8, pp. 2797-2805 (Aug. 2006).
Park, Yoonkyung et al., "A Leu-Lys-rich antimicrobial peptide: activity and mechanism," Biochimica et Biophysica Acta, vol. 1645, pp. 172-182, (2003).
Lehrer, Robert I. et al., "Modulation of the In Vitro Candidacidal Activity of Human Neutrophil Defensins by Target Cell Metabolism and Divalent Cations," Journal of Clinical Investigation, vol. 81, pp. 1829-1835 (Jun. 1988).
Hong, Sung Yu et al., "The effect of charge increase on the specificity and activity of a short antimicrobial peptide," Peptides, vol. 22, pp. 1669-1674 (2001).

* cited by examiner

*Primary Examiner* — Amber D Steele
(74) *Attorney, Agent, or Firm* — Janet Sleath; Speckman Law Group PLLC

(57) ABSTRACT

The present invention relates to peptides for use as antifungal agents. The peptides comprise a sequence of 5 to 15 basic amino acids wherein substantially all of the amino acids in said sequence are the same.

20 Claims, No Drawings

SEQUENCE LISTING

<160> NUMBER OF SEQ ID NOS: 50

<210> SEQ ID NO 1
<211> LENGTH: 7
<212> TYPE: PRT
<213> ORGANISM: Artificial
<220> FEATURE:
<223> OTHER INFORMATION: Synthetic peptide

<400> SEQUENCE: 1

Lys Lys Lys Lys Lys Lys Lys
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Arg Val Arg Val Arg
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Arg Arg Val Val Arg
1               5

<210> SEQ ID NO 4
<211> LENGTH: 5
<212> TYPE: PRT
<213> ORGANISM: Artificial
<220> FEATURE:
<223> OTHER INFORMATION: synthetic peptide

<400> SEQUENCE: 4

Arg Arg Val Arg Arg
1               5

<210> SEQ ID NO 5
<211> LENGTH: 6
<212> TYPE: PRT
<213> ORGANISM: Artificial
<220> FEATURE:
<223> OTHER INFORMATION: synthetic peptide

<400> SEQUENCE: 5

Arg Arg Val Arg Val Arg
1               5

<210> SEQ ID NO 6
<211> LENGTH: 6
<212> TYPE: PRT
<213> ORGANISM: Artificial
<220> FEATURE:
<223> OTHER INFORMATION: synthetic peptide

<400> SEQUENCE: 6

Arg Arg Val Val Arg Arg
1               5

<210> SEQ ID NO 7
<211> LENGTH: 7
<212> TYPE: PRT
<213> ORGANISM: Artificial
<220> FEATURE:
<223> OTHER INFORMATION: synthetic peptide

<400> SEQUENCE: 7

Arg Arg Arg Val Arg Arg Arg
1               5

<210> SEQ ID NO 8
<211> LENGTH: 7
<212> TYPE: PRT
<213> ORGANISM: Artificial
<220> FEATURE:
<223> OTHER INFORMATION: synthetic peptide

<400> SEQUENCE: 8

Arg Arg Val Arg Val Arg Arg
1               5

<210> SEQ ID NO 9
<211> LENGTH: 8
<212> TYPE: PRT
<213> ORGANISM: Artificial
<220> FEATURE:
<223> OTHER INFORMATION: synthetic peptide

<400> SEQUENCE: 9

Arg Arg Arg Val Val Arg Arg Arg
1               5

<210> SEQ ID NO 10
<211> LENGTH: 8
<212> TYPE: PRT
<213> ORGANISM: Artificial
<220> FEATURE:
<223> OTHER INFORMATION: synthetic peptide

<400> SEQUENCE: 10

Arg Arg Val Arg Arg Val Arg Arg
1               5

<210> SEQ ID NO 11
<211> LENGTH: 10
<212> TYPE: PRT
<213> ORGANISM: Artificial
<220> FEATURE:
<223> OTHER INFORMATION: synthetic peptide

<400> SEQUENCE: 11

Arg Arg Arg Arg Val Val Arg Arg Arg Arg
1               5                   10

```
<210> SEQ ID NO 12
<211> LENGTH: 10
<212> TYPE: PRT
<213> ORGANISM: Artificial
<220> FEATURE:
<223> OTHER INFORMATION: synthetic peptide

<400> SEQUENCE: 12

Arg Arg Val Val Arg Arg Val Val Arg Arg
1               5                   10

<210> SEQ ID NO 13
<211> LENGTH: 9
<212> TYPE: PRT
<213> ORGANISM: Artificial
<220> FEATURE:
<223> OTHER INFORMATION: synthetic peptide

<400> SEQUENCE: 13

Arg Arg Arg Arg Arg Arg Arg Arg Arg
1               5

<210> SEQ ID NO 14
<211> LENGTH: 11
<212> TYPE: PRT
<213> ORGANISM: Artificial
<220> FEATURE:
<223> OTHER INFORMATION: synthetic peptide

<400> SEQUENCE: 14

Arg Arg Arg Arg Arg Arg Arg Arg Arg Arg Arg
1               5                   10

<210> SEQ ID NO 15
<211> LENGTH: 13
<212> TYPE: PRT
<213> ORGANISM: Artificial
<220> FEATURE:
<223> OTHER INFORMATION: synthetic peptide

<400> SEQUENCE: 15

Arg Arg Arg Arg Arg Arg Arg Arg Arg Arg Arg Arg Arg
1               5                   10

<210> SEQ ID NO 16
<211> LENGTH: 15
<212> TYPE: PRT
<213> ORGANISM: Artificial
<220> FEATURE:
<223> OTHER INFORMATION: synthetic peptide

<400> SEQUENCE: 16

Arg Arg Arg Arg Arg Arg Arg Arg Arg Arg Arg Arg Arg Arg Arg
1               5                   10                  15

<210> SEQ ID NO 17
<211> LENGTH: 5
<212> TYPE: PRT
<213> ORGANISM: Artificial
<220> FEATURE:
<223> OTHER INFORMATION: synthetic peptide

<400> SEQUENCE: 17

Arg Trp Arg Trp Arg
1               5

<210> SEQ ID NO 18
```

```
<211> LENGTH: 5
<212> TYPE: PRT
<213> ORGANISM: Artificial
<220> FEATURE:
<223> OTHER INFORMATION: synthetic peptide

<400> SEQUENCE: 18

Arg Arg Trp Trp Arg
1               5

<210> SEQ ID NO 19
<211> LENGTH: 5
<212> TYPE: PRT
<213> ORGANISM: Artificial
<220> FEATURE:
<223> OTHER INFORMATION: synthetic peptide

<400> SEQUENCE: 19

Arg Arg Trp Arg Arg
1               5

<210> SEQ ID NO 20
<211> LENGTH: 6
<212> TYPE: PRT
<213> ORGANISM: Artificial
<220> FEATURE:
<223> OTHER INFORMATION: synthetic peptide

<400> SEQUENCE: 20

Arg Arg Trp Arg Trp Arg
1               5

<210> SEQ ID NO 21
<211> LENGTH: 6
<212> TYPE: PRT
<213> ORGANISM: Artificial
<220> FEATURE:
<223> OTHER INFORMATION: synthetic peptide

<400> SEQUENCE: 21

Arg Arg Trp Trp Arg Arg
1               5

<210> SEQ ID NO 22
<211> LENGTH: 7
<212> TYPE: PRT
<213> ORGANISM: Artificial
<220> FEATURE:
<223> OTHER INFORMATION: synthetic peptide

<400> SEQUENCE: 22

Arg Arg Arg Trp Arg Arg Arg
1               5

<210> SEQ ID NO 23
<211> LENGTH: 7
<212> TYPE: PRT
<213> ORGANISM: Artificial
<220> FEATURE:
<223> OTHER INFORMATION: synthetic peptide

<400> SEQUENCE: 23

Arg Arg Trp Arg Trp Arg Arg
1               5

<210> SEQ ID NO 24
<211> LENGTH: 8
```

```
<212> TYPE: PRT
<213> ORGANISM: Artificial
<220> FEATURE:
<223> OTHER INFORMATION: synthetic peptide

<400> SEQUENCE: 24

Arg Arg Arg Trp Trp Arg Arg Arg
1               5

<210> SEQ ID NO 25
<211> LENGTH: 8
<212> TYPE: PRT
<213> ORGANISM: Artificial
<220> FEATURE:
<223> OTHER INFORMATION: synthetic peptide

<400> SEQUENCE: 25

Arg Arg Trp Arg Arg Trp Arg Arg
1               5

<210> SEQ ID NO 26
<211> LENGTH: 10
<212> TYPE: PRT
<213> ORGANISM: Artificial
<220> FEATURE:
<223> OTHER INFORMATION: synthetic peptide

<400> SEQUENCE: 26

Arg Arg Arg Arg Trp Trp Arg Arg Arg Arg
1               5                   10

<210> SEQ ID NO 27
<211> LENGTH: 10
<212> TYPE: PRT
<213> ORGANISM: Artificial
<220> FEATURE:
<223> OTHER INFORMATION: synthetic peptide

<400> SEQUENCE: 27

Arg Arg Trp Trp Arg Arg Trp Trp Arg Arg
1               5                   10

<210> SEQ ID NO 28
<211> LENGTH: 12
<212> TYPE: PRT
<213> ORGANISM: Artificial
<220> FEATURE:
<223> OTHER INFORMATION: synthetic peptide

<400> SEQUENCE: 28

Gly Lys Lys Glu Lys Pro Glu Lys Lys Val Lys Lys
1               5                   10

<210> SEQ ID NO 29
<211> LENGTH: 16
<212> TYPE: PRT
<213> ORGANISM: Artificial
<220> FEATURE:
<223> OTHER INFORMATION: synthetic peptide

<400> SEQUENCE: 29

Lys Leu Thr Lys Pro Lys Pro Gln Ala Glu Ser Lys Lys Lys Lys Lys
1               5                   10                  15

<210> SEQ ID NO 30
<211> LENGTH: 15
<212> TYPE: PRT
```

```
<213> ORGANISM: Artificial
<220> FEATURE:
<223> OTHER INFORMATION: synthetic peptide

<400> SEQUENCE: 30

Lys Lys Lys Lys Lys Glu Gly Lys Lys Gln Glu Lys Met Leu Asp
1               5                   10                  15

<210> SEQ ID NO 31
<211> LENGTH: 8
<212> TYPE: PRT
<213> ORGANISM: Artificial
<220> FEATURE:
<223> OTHER INFORMATION: synthetic peptide

<400> SEQUENCE: 31

Lys Lys Lys Asp Lys Val Lys Lys
1               5

<210> SEQ ID NO 32
<211> LENGTH: 11
<212> TYPE: PRT
<213> ORGANISM: Artificial
<220> FEATURE:
<223> OTHER INFORMATION: synthetic peptide

<400> SEQUENCE: 32

Lys Val Arg Gln Gly Thr Leu Lys Lys Ala Arg
1               5                   10

<210> SEQ ID NO 33
<211> LENGTH: 16
<212> TYPE: PRT
<213> ORGANISM: Artificial
<220> FEATURE:
<223> OTHER INFORMATION: synthetic peptide

<400> SEQUENCE: 33

Pro Lys Thr Lys Ala Lys Ala Lys Ala Lys Lys Gly Lys Gly Lys Asp
1               5                   10                  15

<210> SEQ ID NO 34
<211> LENGTH: 13
<212> TYPE: PRT
<213> ORGANISM: Artificial
<220> FEATURE:
<223> OTHER INFORMATION: synthetic peptide

<400> SEQUENCE: 34

Arg Arg Arg Arg Arg Arg Arg Arg Arg Arg Arg Arg Arg
1               5                   10

<210> SEQ ID NO 35
<211> LENGTH: 5
<212> TYPE: PRT
<213> ORGANISM: Artificial
<220> FEATURE:
<223> OTHER INFORMATION: synthetic peptide

<400> SEQUENCE: 35

Lys Lys Lys Lys Lys
1               5

<210> SEQ ID NO 36
<211> LENGTH: 9
<212> TYPE: PRT
<213> ORGANISM: Artificial
```

```
<220> FEATURE:
<223> OTHER INFORMATION: synthetic peptide

<400> SEQUENCE: 36

Lys Lys Lys Lys Lys Lys Lys Lys Lys
1               5

<210> SEQ ID NO 37
<211> LENGTH: 11
<212> TYPE: PRT
<213> ORGANISM: Artificial
<220> FEATURE:
<223> OTHER INFORMATION: synthetic peptide

<400> SEQUENCE: 37

Lys Lys Lys Lys Lys Lys Lys Lys Lys Lys Lys
1               5                   10

<210> SEQ ID NO 38
<211> LENGTH: 13
<212> TYPE: PRT
<213> ORGANISM: Artificial
<220> FEATURE:
<223> OTHER INFORMATION: synthetic peptide

<400> SEQUENCE: 38

Lys Lys Lys Lys Lys Lys Lys Lys Lys Lys Lys Lys Lys
1               5                   10

<210> SEQ ID NO 39
<211> LENGTH: 15
<212> TYPE: PRT
<213> ORGANISM: Artificial
<220> FEATURE:
<223> OTHER INFORMATION: synthetic peptide

<400> SEQUENCE: 39

Lys Lys Lys Lys Lys Lys Lys Lys Lys Lys Lys Lys Lys Lys Lys
1               5                   10                  15

<210> SEQ ID NO 40
<211> LENGTH: 8
<212> TYPE: PRT
<213> ORGANISM: Artificial
<220> FEATURE:
<223> OTHER INFORMATION: synthetic peptide

<400> SEQUENCE: 40

Arg Phe Trp Trp Phe Arg Arg Arg
1               5

<210> SEQ ID NO 41
<211> LENGTH: 12
<212> TYPE: PRT
<213> ORGANISM: Artificial
<220> FEATURE:
<223> OTHER INFORMATION: synthetic peptide

<400> SEQUENCE: 41

Ile Leu Arg Trp Pro Trp Trp Pro Trp Arg Arg Lys
1               5                   10

<210> SEQ ID NO 42
<211> LENGTH: 12
<212> TYPE: PRT
<213> ORGANISM: Artificial
<220> FEATURE:
```

<223> OTHER INFORMATION: synthetic peptide

<400> SEQUENCE: 42

Ala Lys Arg His His Gly Tyr Lys Arg Lys Phe His
1               5                   10

<210> SEQ ID NO 43
<211> LENGTH: 5
<212> TYPE: PRT
<213> ORGANISM: Artificial
<220> FEATURE:
<223> OTHER INFORMATION: synthetic peptide

<400> SEQUENCE: 43

Arg Arg Arg Arg Arg
1               5

<210> SEQ ID NO 44
<211> LENGTH: 7
<212> TYPE: PRT
<213> ORGANISM: Artificial
<220> FEATURE:
<223> OTHER INFORMATION: synthetic peptide

<400> SEQUENCE: 44

Arg Arg Arg Arg Arg Arg Arg
1               5

<210> SEQ ID NO 45
<211> LENGTH: 5
<212> TYPE: PRT
<213> ORGANISM: Artificial
<220> FEATURE:
<223> OTHER INFORMATION: synthetic peptide

<400> SEQUENCE: 45

His His His His His
1               5

<210> SEQ ID NO 46
<211> LENGTH: 7
<212> TYPE: PRT
<213> ORGANISM: Artificial
<220> FEATURE:
<223> OTHER INFORMATION: synthetic peptide

<400> SEQUENCE: 46

His His His His His His His
1               5

<210> SEQ ID NO 47
<211> LENGTH: 9
<212> TYPE: PRT
<213> ORGANISM: Artificial
<220> FEATURE:
<223> OTHER INFORMATION: synthetic peptide

<400> SEQUENCE: 47

His His His His His His His His His
1               5

<210> SEQ ID NO 48
<211> LENGTH: 11
<212> TYPE: PRT
<213> ORGANISM: Artificial
<220> FEATURE:
<223> OTHER INFORMATION: synthetic peptide

```
<400> SEQUENCE: 48

His His His His His His His His His His
1               5                   10

<210> SEQ ID NO 49
<211> LENGTH: 13
<212> TYPE: PRT
<213> ORGANISM: Artificial
<220> FEATURE:
<223> OTHER INFORMATION: synthetic peptide

<400> SEQUENCE: 49

His His His His His His His His His His His His His
1               5                   10

<210> SEQ ID NO 50
<211> LENGTH: 15
<212> TYPE: PRT
<213> ORGANISM: Artificial
<220> FEATURE:
<223> OTHER INFORMATION: synthetic peptide

<400> SEQUENCE: 50

His His His His His His His His His His His His His His His
1               5                   10                  15
```

PEPTIDES AND THEIR USE

REFERENCE TO RELATED APPLICATIONS

This application is the US national phase entry of International Patent Application No. PCT/GB2008/000283, filed Jan. 28, 2008, which claims priority to GB Patent Application No. 0702020.9, filed Feb. 2, 2007, and U.S. Provisional Patent Application No. 60/899,283, filed Feb. 2, 2007.

FIELD OF THE INVENTION

This invention relates to peptides and their use in the treatment of fungal infections.

BACKGROUND TO THE INVENTION

Systemic fungal diseases (systemic mycoses) are generally chronic, very slowly induced by opportunistic causative fungi which may not normally be pathogenic but represent a major threat to susceptible patients. Susceptible individuals are those with primary (inherent) immunodeficiencies, those hospitalised or living long term with indwelling surgical devices (e.g. catheters, Hickman and central lines), those undergoing invasive surgical techniques and those with secondary immunodeficiencies as a result of HIV infection, immunoablative chemotherapy or ionising irradiation, corticosteroids or other immunosuppressive drugs, prolonged exposure to antimicrobial agents etc.

Life threatening systemic fungal infections are those in which the pathogenic organisms of the blood stream, lungs and other mucosal tissue, the liver and immune sites such as the lymph glands and spleen. The diagnosis of specific fungal diseases may be made by isolation of the causative fungus from sputum, urine, blood, or the bone marrow, or with prevalent fungus types by evidence of tissue invasion. Superficial fungal infections are generally caused by dermatophytes that involve the outer layers of the skin, hair or nails. The infections may result in a mild inflammation, and cause intermittent remissions and exacerbations of a gradually extending, scaling, raised lesion. Yeasts and moulds do not generally give rise to systemic infections in healthy individuals only in immunocompromised individuals, however healthy individuals can suffer from superficial infections. Yeast infections including oral candidiasis (oral thrush) are usually restricted to the skin, and mucous membranes although yeast infections can also be systemic. Commonly, infections appear as erythematous, often itchy, exudative patches in the axillas, umbilicus, groin, between toes, and on finger-webs. Oral thrush involves an inflamed tongue, or buccal mucosa and presents as white patches of exudate, while chronic mucocutaneous candidiasis is characterized by red, pustular, crusted, thickened lesions on the forehead or nose. *C. albicans* can cause superficial infections of the vaginal cavity of healthy individuals; indeed up to three quarters of all women will suffer at least one episode of vaginal thrush during their lifetime. Most of these women experience infrequent attacks and respond well to drug therapy, however in some the infection is recurrent or persistent and does not respond to drug therapy.

The treatment options for infections contributed to or caused by fungi (including yeast) are severely limited and there is an urgent need to discover new therapies which inhibit or kill such organisms.

In our co-pending application, WO 2006/018652, we describe the identification of peptides that can be used to treat microbial infections in particular dermatophytic infections such as onychomycosis. For the peptides described therein, antimicrobial activity was generally confined to large cationic peptides comprising from 28 up to 200 or more basic amino acids.

SUMMARY OF THE INVENTION

The present invention is based in part on the finding that smaller peptides of between 5 and 15 arginine residues are highly fungicidal and as such are effective in the treatment of certain fungal infections in particular systemic fungal and yeast infections. Without wishing to be bound by theory, it is believed that, in one mode of action, the peptides can insert into the negatively charged cytoplasmic membrane of the fungus leading to cell lysis and/or a breakdown in membrane integrity and subsequently, microbial death.

According to a first aspect the invention provides a peptide for use as an antifungal agent wherein the peptide comprises a sequence of 5 to 15 basic amino acids wherein substantially all of the amino acids in said sequence are the same.

In a preferred peptide the basic amino acids are selected from lysine, arginine and histidine, in particular lysine and arginine. Preferably still the basic amino acid is arginine.

As used herein "substantially" is a relative modifier intended to indicate permissible variation from the characteristic so modified. Specifically, by "substantially all of the amino acids in said sequence of 5 to 15 amino acids are the same" it is meant that either all, or a high proportion of, the amino acids in the sequence are identical. By "high proportion" it is contemplated that 1 or 2 substitutions may be made in the sequence.

Peptides according to the invention have advantages over respective peptides of more than 15 amino acid residues since they peptides do not have associated synthesis and cell toxicity issues.

In a preferred aspect the peptide of the invention comprises a sequence of 9 to 15, for example 11 to 15, basic amino acids wherein substantially all of the amino acids in said sequence of amino acids are the same. Preferably still the peptide of the invention comprises a sequence of 9 to 13, for example 11 to 13, basic amino acids wherein substantially all of the amino acids in said sequence are the same.

Thus the present invention provides a peptide, or a peptide variant thereof, comprising an amino acid sequence according to the formula (I)

$$(X)_n \qquad\qquad (I)$$

wherein X is each of arginine or lysine and n is an integer between 5 and 15, for use as an antifungal agent.

In a preferred peptide of the invention X is arginine.

In an alternative preferred peptide of the invention X is lysine.

In a peptide of the invention n may be between 9 and 15 e.g. 9, 10, 11, 12, 13, 14 or 15. In a preferred peptide of the invention n is an integer between 11 and 15, for example between 11 and 14. Preferably n is 13 or 14. Preferably still n is 13.

In an alternative preferred peptide of the invention n is an integer between 9 and 13, for example between 11 and 13. Preferably still n is between 9 and 11.

In a peptide of formula (I), X may be a D- or L-amino acid.

In a preferred aspect the invention provides a linear peptide consisting of amino acids according to formula (I).

The invention also includes known isomers (structural, stereo-, conformational & configurational) and structural analogues of the above amino acids, including peptidomimetics, and those modified either naturally (e.g. post-translational modification) or chemically, including, but not exclusively, phosphorylation, glycosylation, sulfonylation and/or hydroxylation.

In addition, the amino acid sequence of the peptide can be modified so as to result in a peptide variant that includes the substitution of at least one (for example one or two) amino acid residue in the peptide for another amino acid residue including substitutions that utilise the D rather than L form, wherein the variant retains some (typically at least 10%) or all of the biological activity of the corresponding non-variant peptide. Thus the invention provides a peptide variant in which one or more lysine or arginine residues of formula (I) is substituted by one or more residues other residues, for example a basic residues such as histidine.

The term "peptide" as used herein means, in general terms, a plurality of amino acid residues joined together by peptide bonds. It is used interchangeably and means the same as polypeptide and protein.

The peptides of the invention generally are synthetic peptides. The peptides may be isolated, purified peptides or variants thereof, which can be synthesised in vitro, for example, by a solid phase peptide synthetic method, by enzyme-catalysed peptide synthesis or with the aid of recombinant DNA technology.

The peptides of the invention can exist in different forms, such as free acids, free bases, esters and other prodrugs, salts and tautomers, for example, and the invention includes all variant forms of the peptides. Thus, the invention encompasses the salt or pro-drug of a peptide.

The peptide of the invention may be administered in the form of a pharmaceutically acceptable salt. The invention thus includes pharmaceutically-acceptable salts of the peptide of the invention wherein the parent compound is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glutamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Salts of carboxyl groups of a peptide or peptide variant of the invention may be prepared in the usual manner by contacting the peptide with one or more equivalents of a desired base such as, for example, a metallic hydroxide base, e.g. sodium hydroxide; a metal carbonate or bicarbonate such as, for example, sodium carbonate or bicarbonate; or an amine base such as, for example, triethylamine, triethanolamine and the like.

Administration and Pharmaceutical Formulations

A further aspect of the invention provides a pharmaceutical composition comprising a pharmaceutically effective amount of a peptide of the invention.

The composition also includes a pharmaceutically acceptable carrier, excipient or diluent. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

To achieve the desired effect(s), the peptide, a variant thereof or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight or at least about 1 mg/kg to about 20 mg/kg of body weight, although other dosages may provide beneficial results.

To prepare the composition, peptides are synthesised or otherwise obtained, purified as necessary or desired, and then lyophilised and stabilised. The peptide can then be adjusted to the appropriate concentration and optionally combined with other agents.

Thus, one or more suitable unit dosage forms comprising the therapeutic peptides of the invention can be administered by a variety of routes including oral, topical, parenteral (including subcutaneous, intravenous, intramuscular and intraperitoneal), vaginal, rectal, dermal, transdermal, intrathoracic, intrapulmonary and intranasal (respiratory) routes.

When the therapeutic peptides of the invention are prepared for oral administration, they are generally combined with a pharmaceutically acceptable carrier, diluent or excipient to form a pharmaceutical formulation, or unit dosage form. For oral administration, the peptides may be present as a powder, a granular formation, a solution, a suspension or an emulsion.

Pharmaceutical formulations containing the therapeutic peptides of the invention can be formulated with common excipients, diluents, or carriers, and formed into tablets, capsules, solutions, suspensions, powders, aerosols and the like.

The therapeutic peptides of the invention can also be formulated as elixirs or solutions for convenient oral administration or as solutions appropriate for parenteral administration, for instance by intramuscular, subcutaneous, intraperitoneal or intravenous routes.

These formulations can contain pharmaceutically acceptable carriers, vehicles and adjuvants that are well-known in the art. It is possible, for example, to prepare solutions using one or more organic solvent(s) that is/are acceptable from the physiological standpoint, chosen, in addition to water, from solvents such as acetone, acetic acid, ethanol, isopropyl alcohol, dimethyl sulphoxide, glycol ethers such as the products sold under the name "Dowanol", polyglycols and polyethylene glycols, $C_1$-$C_4$ alkyl esters of short-chain acids, ethyl or isopropyl lactate, fatty acid triglycerides such as the products marketed under the name "Miglyol", isopropyl mytrisate, animal, mineral and vegetable oils and polysiloxanes.

Also contemplated are products that include one or more peptides of the present invention in combination with one or more other antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents. In addition, it is contemplated that the peptides might be combined with topical antifungal agents such as ciclopirox olamine, haloprogin, tolnaftate, undecylenate, topical nysatin, amorolfine, butenafine, naftifine, terbinafine, and other topical agents.

For topical administration, the active agents may be formulated as is known in the art for direct application to a target area, for example nails and skin. Forms chiefly conditioned for topical application take the form, for example, of laquers, creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic peptides of the invention can be delivered via patches or bandages for dermal administration.

The peptides of the invention may be administered vaginally for example in the form of a pessary or suppository.

The peptides of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Use

The peptides of the invention may be useful in the treatment or prevention of fungal infections, including yeast and mould infections.

Thus a further aspect of the invention provides the use of a peptide according to the invention, or a pharmaceutically acceptable salt thereof, in the manufacture of a medicament for the treatment or alleviation of an infection contributed to or caused by a fungus.

The infection to be treated may be a dermatophyte infection such as an infection caused by a fungus of the genus *Trichophyton* spp for example *Trichophyton rubrum*.

Preferably the infection to be treated is a non-dermatophyte infection. The fungal infection may be caused by, but not exclusive to, a fungus selected from the group consisting of *Absidia* spp, (e.g. *Absidia corymbifera*), *Aspergillus* spp, (e.g. *Aspergillus candidus, Aspergillus niger, Aspergillus tamarii, Aspergillus flavus, Aspergillus fumigatus, Aspergillus sydowii, Aspergillus terreus, Aspergillus ustus, Aspergillus versicolor, Aspergillus clavatus, Aspergillus glaucus* group, *Aspergillus nidulans, Aspergillus oryzae*), *Cryptococcus* spp (e.g. *Crytococcus neoformans* var. *neoformans, Crytococcus neoformans* var. *gatii, Crytococcus neoformans* var. *grubii*), *Malassezia* spp (e.g. *Malassezia furfur, Malassezia pachydermatis, Malassezia globosa, Malassezia obtuse, Malassezia restricta, Malassezia slooffiae, Malassezia sympodialis*), *Candida* spp (e.g. *Candida albicans, Candida tropicalis, Candida glabrata, Candida parapsilosis, Candida krusei, Candida lusitaniae, Candida kefyr, Candida sake, Candida guilliermondii, Candida dubliniensis, Candida ciferii, Candida famata, Candida lambica, Candida lipolytica, Candida norvegensis, Candida rugosa, Candida viswanathii, Candida zeylanoides*), *Rhizomucor* spp, (e.g. *Rhizomucor pusillus, Rhizomucor miehei, Rhizomucor variabilis*), *Saccharomyces* spp, (e.g. *Saccharomyces cerevisiae, Saccharomyces boullardii*), *Hansenula* spp, *Fusarium* spp (e.g. *Fusarium oxysporum, Fusarium solani, Fusarium chlamydosporum, Fusarium moniliforme, Fusarium proliferatum*), *Mucor* spp (e.g. *Mucor amphibiorum, Mucor circinelloides, Mucor hiemalis, Mucor indicus, Mucor racemosus, Mucor ramosissimus*), *Trichosporon* spp (e.g. *Trichosporon beigelii, Trichosporon cutaneum, Trichosporon asteroids, Trichosporon ovoides, Trichosporon inikin, Trichosporon asahii, Trichosporon mucoides*), *Rhodotorula* spp, (e.g. *Rhodotorula glutinis, Rhodotorula minuta, Rhodotorula mucilaginosa*), *Pichia* spp, (e.g. *Pichia anomola, Pichia guilliermondii, Pichia norvegensis, Pichia ohmerii*), *Rhizopus* spp., (e.g. *Rhizopus arrhizus, Rhizopus microsporus*), *Penicillium* spp (e.g. *Penicillium marneffei, Penicillium verrucosum*), *Scopulariopsis* spp., (e.g. *Scopulariopsis brevicaulis*) and *Blastoschizomyces* spp (e.g. *Blastoschizomyces capitatus*).

The fungus may be an obligate or opportunistic pathogen. Preferably the fungus is an opportunistic pathogen.

In a preferred use according to the invention the fungal infection is caused by a fungus/yeast selected from *Aspergillus* spp., *Fusarium* spp., *Candida* spp., *Alternaria* spp., *Malassezia* spp., *Scopulariopsis* spp. *Cryptococcus* spp., or *Penicillium* spp.

In a preferred use according to the invention the fungal infection is caused by a yeast, for example *Candida* spp.

In a preferred use according to the invention the fungal infection is caused by *Aspergillus* spp. In a preferred embodiment the fungal infection is caused by *Aspergillus niger* or *Aspergillus nidulans*.

In a preferred use according to the invention the fungal infection is caused by *Fusarium* spp.

In a preferred use according to the invention the fungal infection is caused by *Alternaria* spp.

In a preferred use according to the invention the fungal infection is caused by *Malassezia* spp.

In a preferred use according to the invention the fungal infection is caused by *Penicillium* spp.

In a preferred use according to the invention the fungal infection is caused by *Scopulariopsis* spp.

In a preferred use according to the invention the fungal infection is caused by *Cryptococcus* spp.

The invention further provides the use of a peptide of the invention, or a pharmaceutically acceptable salt thereof, in the manufacture of a medicament for the treatment or alleviation of a disease or condition contributed to or caused by a fungal infection.

The disease or condition, herein referred to as a "mycosis", may be a superficial mycosis, a subcutaneous mycosis or a systemic mycosis. Superficial mycoses may include tinea infections (e.g. tinea barbae, tinea capitis, tinea corporis, tinea cruris, tinea favosa, tinea nigra, tinea pedis, tinea manuum, tinea imbricate), pityriasis versicolor, white piedra, black piedra, dermatophytoses (ringworm) and candidiasis of the skin, nails or mucous membranes.

Subcutaneous mycoses may include sporotrichosis, chromoblastomycosis and mycetoma.

Preferably the disease or condition to be treated is a systemic mycosis. Examples of systemic mycoses include candidaemia, histoplasmosis, coccidioidomycosis, blastomycosis, paracoccidioidomycosis, aspergillosis, candidiasis, fusariosis, cryptococcosis, phaeohyphomycosis, hyalohyphomycosis, mucormycosis and chromomycosis.

The systemic mycosis is selected from the group consisting of candidaemia, aspergillosis, fusariosis, candidiasis, alternariosis, fungemia and cryptococcosis.

In a preferred aspect of the invention the disease or condition to be treated is an opportunistic systemic mycosis for example a systemic mycosis selected from the group consisting of, but not limited to, candidaemia, aspergillosis, alternariosis, candidiasis, fusariosis, and cryptococcosis.

Clinical diseases or conditions that may be contributed to or caused by mycoses include, but are not limited to, candidaemia, pneumonia, endocarditis, onychomycosis, meningitis, encephalitis, urinary tract infection, mycetoma, pneumothorax, aspergillosis, hyalohyphomycosis, cryptococcosis (meningoencephalitis), versicolor, candidiasis, dermatitis, folliculitis, postulosis (in neonates), blepharitis, white piedra, black piedra, acne vulgaris, septicaemia, peritonitis, thrush, vulvovaginitis, empyema, liver abscess, trichosporonosis, blastomycosis, coccidioidomycosis, histoplasmosis, paracoccidiomycosis, sporotrichosis, zygomycosis, chromoblastomycosis, eye infections, lobomycosis, mycetoma, nail, hair, and skin disease, otomycosis, osteomyelitis phaeohyphomycosis, rhinosporidiosis, mucormycosis.

Major clinical diseases in immunocompromised hosts that are contributed to or caused by systemic mycoses include, but are not limited to, candidaemia, pneumonia, candidiasis (including oropharyngeal and esophageal candidiasis), pulmonary aspergillosis, cerebral infection, rhinosinusitis, pulmonary crytococcosis, meningitis, rhinocerebral mucormycosis and pulmonary mucormycosis.

Disease or conditions that are contributed to or caused by an infection by *aspergillus* spp. include aspergillosis, otomycosis, osteomyelitis, sinus disease, pulmonary disease and nasoorbital infections. *Aspergillus* spp. primarily affects immunocompromised hosts such as leukemia or transplant (e.g. bone marrow) patients.

Disease or conditions that are contributed to or caused by an infection by *fusarium* spp. include keratitis, endophthalmitis, otitis media, onychomycosis, cutaneous infections (in particular burn wounds), mycetoma, sinusitis, pulmonary infections, endocarditis, peritonitis, venous catheter infections, septic arthritis, disseminated infections and fungemia.

Disease or conditions that are contributed to or caused by an infection by *alternaria* spp. include bronchial asthma and alternariosis of the skin or lung.

Disease or conditions that are contributed to or caused by an infection by *Cryptococcus* spp., for example *Cryptococcus neoformans*, include wound or cutaneous cryptococcosis, pulmonary cryptococcosis or cryptococcal meningitis.

The diseases or disorders to be treated may be nosocomial disorders.

In one embodiment the invention provides the use of a peptide of formula (I) wherein n is an integer between 11 and 15 (in particular between 11 and 13), or a pharmaceutically acceptable salt thereof, in the manufacture of a medicament for the treatment of opportunistic systemic mycoses.

The peptides of the invention are useful in the treatment of yeast and mould infections in immunocompromised and non-immunocompromised patients. The majority of yeasts and moulds are pathogenic in immunocompromised patients, for example, patients compromised by HIV infection, cancer chemotherapy, indwelling surgical devices (e.g. catheters), ionizing irradiation, corticosteroids, immunosuppressives for example in organ or bone marrow transplantation, invasive surgical techniques, prolonged exposure to antibiotics, or by diseases or conditions such as cancer, leukemia, emphysema, bronchiectasis, diabetes mellitus, burns, and the like.

Yeast and mould infections that are pathogenic in immunocompromised patients include fungaemia (of the bloodstream lungs, kidneys, liver, spleen, brain and endocardium), candidaemia, candidiasis, pneumonia, ostoemyelitis, discitis, cryptococcosis (pulmonary, skin, prostate and medullary cavity), catheter related infections, mycoses including meningitis, septicaemia and peritonitis, sepsis, white piedra and trichosporonosis.

Fungal infections according to the invention may be local or systemic infections. Local infections caused by *Candida* spp include thrush e.g. oral thrush, oesophagitis, cutaneous candidiasis, vaginal thrush. Such local infections may be treatable by formulations such as tablets, creams, ointments, suppositories comprising a peptide, or pharmaceutically acceptable salt thereof, of the invention.

Yeast and mould infections treatable by the peptides of the present invention may be selected from any of the infections, and their causative pathogens, shown in Table 2.

A further aspect of the invention provides a method for the treatment, prevention or delay of progression of a mycosis which comprises administering to a patient a therapeutically effective amount of a peptide according to the invention, or a pharmaceutically acceptable salt thereof.

Preferably the patient is a mammal, in particular human.

The mycoses treatable by a method of the invention may be a systemic mycoses for example an opportunistic systemic mycoses. In a preferred method of the invention, the peptide, or pharmaceutically acceptable salt thereof, is intended as a formulation intended for inhalation, oral or parenteral administration.

Thus in one embodiment the invention provides a method for the treatment, prevention or delay of progression of a mycosis which comprises administering to a patient a therapeutically effective amount of an aerosol formulation comprising a peptide according to the invention, or a pharmaceutically acceptable salt thereof. The invention further provides an aerosol formulation, including an inhaler comprising said aerosol formulation, comprising a peptide according to the invention, or a pharmaceutically acceptable salt thereof.

In a further embodiment the invention provides a method for the treatment, prevention or delay of progression of a mycosis which comprises administering to a patient a therapeutically effective amount of a parenteral formulation comprising a peptide according to the invention, or a pharmaceutically acceptable salt thereof. The invention further provides a parenteral formulation (in particular intravenous) comprising a peptide according to the invention, or a pharmaceutically acceptable salt thereof.

In a yet further embodiment the invention provides a method for the treatment, prevention or delay of progression of a mycosis which comprises administering to a patient a therapeutically effective amount of an oral formulation comprising a peptide according to the invention, or a pharmaceutically acceptable salt thereof. The invention further provides an oral formulation comprising a peptide according to the invention, or a pharmaceutically acceptable salt thereof.

The diagnosis of specific diseases or conditions treatable according to the invention can be readily determined by the skilled person by the isolation of the causative fungus from blood, tissue, urine etc followed by assaying the fungicidal/fungistatic effect of the peptide.

The extent of protection includes counterfeit or fraudulent products which contain or purport to contain a compound of the invention irrespective of whether they do in fact contain such a compound and irrespective of whether any such compound is contained in a therapeutically effective amount.

Features, integers, characteristics, compounds, chemical moieties or groups described in conjunction with a particular aspect, embodiment or example of the invention are to be understood to be applicable to any other aspect, embodiment or example described herein unless incompatible therewith.

The following Example illustrates the invention.

EXAMPLE

Materials and Methods

Peptide Synthesis

All peptides were produced either by solid-phase synthesis under contract by a peptide supplier, NeoMPS SA (Strasbourg, France), or purchased from Sigma-Aldrich Chemical Company Ltd. (Poole, UK).

Broth Dilution Antifungal Susceptibility Testing

The sensitivity of relevant fungal strains to the peptides was determined using Clinical Laboratory Standard Institute (CLSI; formerly NCCLS) Approved Standards. Fungal susceptibility was tested using "Reference Method for Broth Dilution Antifungal Susceptibility Testing of Filamentous Fungi; Approved Standard M38-P", and yeast susceptibility was tested using "Reference Method for Broth Dilution Antifungal Susceptibility Testing of Yeasts; Approved Standard—Second Edition M27-A".

DETAILED DESCRIPTION

Results

Sequence of Cationic Peptides

The sequence of the peptides analysed is shown in Table 1. Ac represents an Acetylated modification to the C-terminus of the oligopeptide and $NH_2$ represents an amidation of the N-terminus of the oligopeptide.

TABLE 1

*Candida* spp. Type Strains MIC Data table (µM)

| Peptide | Amino Acid Sequence | |
|---|---|---|
| NP101 | Poly-L-Lysine (MW 15-30 kDa) | |
| NP108 | Poly-L-Lysine (MW 10-20 kDa) | |
| NP112 | Poly-L-Lysine (MW 0.5-2 kDa) | |
| NP121 | Poly-L-Arginine (MW 5-15 kDa) | |
| NP213 | cyclo-KKKKKKK | (SEQ ID NO: 1) |
| NP301 | RVRVR | (SEQ ID NO: 2) |
| NP302 | RRVVR | (SEQ ID NO: 3) |
| NP303 | RRVRR | (SEQ ID NO: 4) |
| NP304 | RRVRVR | (SEQ ID NO: 5) |
| NP305 | RRVVRR | (SEQ ID NO: 6) |
| NP306 | RRRVRRR | (SEQ ID NO: 7) |
| NP307 | RRVRVRR | (SEQ ID NO: 8) |
| NP308 | RRRVVRRR | (SEQ ID NO: 9) |
| NP309 | RRVRRVRR | (SEQ ID NO: 10) |
| NP310 | RRRRWRRRR | (SEQ ID NO: 11) |
| NP311 | RRWRRWRR | (SEQ ID NO: 12) |
| NP316 | RRRRRRRRR | (SEQ ID NO: 13) |
| NP317 | RRRRRRRRRR | (SEQ ID NO: 14) |
| NP318 | RRRRRRRRRRRR | (SEQ ID NO: 15) |
| NP319 | RRRRRRRRRRRRRR | (SEQ ID NO: 16) |
| NP320 | RWRWR | (SEQ ID NO: 17) |
| NP321 | RRWWR | (SEQ ID NO: 18) |
| NP322 | RRWRR | (SEQ ID NO: 19) |
| NP323 | RRWRWR | (SEQ ID NO: 20) |
| NP324 | RRWWRR | (SEQ ID NO: 21) |
| NP325 | RRRWRRR | (SEQ ID NO: 22) |
| NP326 | RRWRWRR | (SEQ ID NO: 23) |
| NP327 | RRRWWRRR | (SEQ ID NO: 24) |
| NP328 | RRWRRWRR | (SEQ ID NO: 25) |
| NP329 | RRRRWWRRRR | (SEQ ID NO: 26) |
| NP330 | RRWWRRWWRR | (SEQ ID NO: 27) |
| NP331 | GKKEKPEKKVKK | (SEQ ID NO: 28) |
| NP332 | KLTKPKPQAESKKKKK | (SEQ ID NO: 29) |
| NP333 | KKKKKEGKKQEKMLD | (SEQ ID NO: 30) |
| NP334 | KKKDKVKK | (SEQ ID NO: 31) |
| NP335 | KVRQGTLKKAR | (SEQ ID NO: 32) |
| NP336 | PKTKAKAKAKKGKGKD | (SEQ ID NO: 33) |
| NP337 | RRRRRRRRRRRR | (SEQ ID NO: 34) |
| NP338 | Ac-RRRRRRRRRRRR-$NH_2$ | (SEQ ID NO: 34) |
| NP339 | dRdRdRdRdRdRdRdRdRdRdRdR | (SEQ ID NO: 34) |
| NP340 | Ac-dRdRdRdRdRdRdRdRdRdRdRdR-$NH_2$ | (SEQ ID NO: 34) |
| NP341 | dRdRdRdRdRdRdRdRdRdRdRdR-CONH | (SEQ ID NO: 34) |
| NP342 | KKK | |
| NP343 | KKKKK | (SEQ ID NO: 35) |
| NP344 | KKKKKKK | (SEQ ID NO: 1) |
| NP345 | KKKKKKKKK | (SEQ ID NO: 36) |
| NP346 | KKKKKKKKKKK | (SEQ ID NO: 37) |
| NP347 | KKKKKKKKKKKKK | (SEQ ID NO: 38) |
| NP348 | KKKKKKKKKKKKKKK | (SEQ ID NO: 39) |
| NP349 | RRRRRRRRR | (SEQ ID NO: 13) |
| NP350 | RRRRRRRRRRR | (SEQ ID NO: 14) |
| NP351 | RRRRRRRRRRRRR | (SEQ ID NO: 15) |

TABLE 1-continued

Candida spp. Type Strains MIC Data table (µM)

| Peptide | Amino Acid Sequence | |
|---|---|---|
| NP352 | RRRRRRRRRRRRRR | (SEQ ID NO: 16) |
| NP353 | dRdFdWdWdFdRdRdR-CONH₂ | (SEQ ID NO: 40) |
| NP354 | ILRWPWWPWRRK-CONH₂ | (SEQ ID NO: 41) |
| NP355 | dAdKdRdHdHdGdYdKdRdKdFdH-CONH₂ | (SEQ ID NO: 42) |
| NP356 | RRR | |
| NP357 | RRRRR | (SEQ ID NO: 43) |
| NP358 | RRRRRR | (SEQ ID NO: 44) |
| NP359 | dHdHdH | |
| NP360 | dHdHdHdHdH | (SEQ ID NO: 45) |
| NP361 | dHdHdHdHdHdHdH | (SEQ ID NO: 46) |
| NP362 | dHdHdHdHdHdHdHdHdH | (SEQ ID NO: 47) |
| NP363 | dHdHdHdHdHdHdHdHdHdHdH | (SEQ ID NO: 48) |
| NP364 | dHdHdHdHdHdHdHdHdHdHdHdHdH | (SEQ ID NO: 49) |
| NP365 | dHdHdHdHdHdHdHdHdHdHdHdHdHdH | (SEQ ID NO: 50) |

Data showing the activity of the peptides against various fungal, including yeast, strains is shown in Table 2.

TABLE 2

Yeast MIC Data

| Genus & Species | Strain | Peptide | MIC (µM) |
|---|---|---|---|
| C. albicans | ATCC24433 | NP323 | 1024 |
| C. albicans | ATCC24433 | NP324 | 1024 |
| C. albicans | ATCC24433 | NP326 | 1024 |
| C. albicans | ATCC24433 | NP327 | 1024 |
| C. albicans | ATCC24433 | NP328 | 2048 |
| C. albicans | ATCC24433 | NP329 | 1024 |
| C. albicans | ATCC24433 | NP337 | 4 |
| C. albicans | ATCC24433 | NP338 | 2 |
| C. albicans | ATCC24433 | NP340 | 8 |
| C. albicans | NCTC3179 | NP342 | >2048 |
| C. albicans | NCTC3179 | NP344 | >2048 |
| C. albicans | NCTC3179 | NP343 | >2048 |
| C. albicans | NCTC3179 | NP344 | >2048 |
| C. albicans | NCTC3179 | NP345 | >2048 |
| C. albicans | NCTC3179 | NP346 | >2048 |
| C. albicans | NCTC3179 | NP347 | >2048 |
| C. albicans | NCTC3179 | NP348 | >2048 |
| C. albicans | NCTC3179 | NP349 | 2048 |
| C. albicans | NCTC3179 | NP350 | 64 |
| C. albicans | NCTC3179 | NP351 | 4 |
| C. albicans | NCTC3179 | NP352 | 4 |
| C. albicans | NCTC3179 | NP356 | >2048 |
| C. albicans | NCTC3179 | NP357 | >2048 |
| C. albicans | NCTC3179 | NP358 | >2048 |
| C. albicans | ATCC90028 | NP323 | 2048 |
| C. albicans | ATCC90028 | NP324 | 1024 |
| C. albicans | ATCC90028 | NP326 | 1024 |
| C. albicans | ATCC90028 | NP327 | 256 |
| C. albicans | ATCC90028 | NP328 | 1024 |
| C. albicans | ATCC90028 | NP337 | 4 |
| C. albicans | ATCC90028 | NP338 | 4 |
| C. albicans | ATCC90028 | NP340 | 2 |
| C. albicans | 73/034 | NP337 | 512 |
| C. albicans | 73/034 | NP338 | 256 |
| C. albicans | 73/034 | NP340 | 2 |
| C. albicans | AM2003-020 | NP337 | 4 |
| C. albicans | AM2003-020 | NP338 | 4 |
| C. albicans | AM2003-020 | NP340 | 2 |
| C. albicans | AM2003-0069 | NP337 | 16 |
| C. albicans | AM2003-0069 | NP338 | 16 |
| C. albicans | AM2003-0069 | NP340 | 2 |
| C. albicans | AM2003-0100 | NP337 | 16 |
| C. albicans | AM2003-0100 | NP338 | 16 |
| C. albicans | AM2003-0100 | NP340 | 2 |
| C. albicans | AM2003-0182 | NP337 | 256 |
| C. albicans | AM2003-0182 | NP338 | 32 |
| C. albicans | AM2003-0182 | NP340 | 4 |
| C. albicans | AM2003-0191 | NP337 | 2 |
| C. albicans | AM2003-0191 | NP338 | 1 |
| C. albicans | AM2003-0191 | NP340 | 4 |
| C. albicans | AM2004-0025 | NP337 | 2 |
| C. albicans | AM2004-0025 | NP338 | 1 |
| C. albicans | AM2004-0025 | NP340 | 4 |
| C. albicans | AM2005-0377 | NP337 | 64 |
| C. albicans | AM2005-0377 | NP338 | 128 |
| C. albicans | AM2005-0377 | NP340 | 2 |
| C. albicans | HUN68 | NP337 | 4 |
| C. albicans | HUN68 | NP338 | 1 |
| C. albicans | HUN68 | NP340 | 4 |
| C. albicans | IHEM3742 | NP337 | 128 |
| C. albicans | IHEM3742 | NP338 | 4 |
| C. albicans | IHEM3742 | NP340 | 2 |
| C. albicans | IHEM16614 | NP337 | 64 |
| C. albicans | IHEM16614 | NP338 | 16 |
| C. albicans | IHEM16614 | NP340 | 2 |
| C. albicans | IHEM16945 | NP337 | 128 |
| C. albicans | IHEM16945 | NP338 | 16 |
| C. albicans | IHEM16945 | NP340 | 4 |
| C. albicans | IHEM16972 | NP337 | 32 |
| C. albicans | IHEM16972 | NP338 | 8 |
| C. albicans | IHEM16972 | NP340 | 2 |
| C. albicans | L1086 | NP337 | 2 |
| C. albicans | L1086 | NP338 | 2 |
| C. albicans | L1086 | NP340 | 2 |
| C. albicans | RV4688 | NP337 | 512 |
| C. albicans | RV4688 | NP338 | 16 |
| C. albicans | RV4688 | NP340 | 512 |
| C. albicans | s20122.073 | NP337 | 2 |
| C. albicans | s20122.073 | NP338 | 2 |
| C. albicans | s20122.073 | NP340 | 2 |
| C. albicans | s20152.013 | NP337 | 256 |
| C. albicans | s20152.013 | NP338 | 32 |
| C. albicans | s20152.013 | NP340 | 4 |
| C. albicans | s20152.082 | NP337 | 128 |
| C. albicans | s20152.082 | NP338 | 16 |
| C. albicans | s20152.082 | NP340 | 4 |
| C. albicans | s20175.016 | NP337 | 512 |
| C. albicans | s20175.016 | NP338 | 128 |
| C. albicans | s20175.016 | NP340 | 0.5 |
| C. albicans | s20176.079 | NP337 | 128 |
| C. albicans | s20176.079 | NP338 | 32 |
| C. albicans | s20176.079 | NP340 | 2 |
| C. krusei | NCPF3953 | NP316 | 32 |
| C. krusei | NCPF3953 | NP317 | 32 |
| C. krusei | NCPF3953 | NP318 | 8 |
| C. krusei | NCPF3953 | NP319 | <16 |
| C. krusei | NCPF3953 | NP323 | 256 |
| C. krusei | NCPF3953 | NP324 | 256 |
| C. krusei | NCPF3953 | NP326 | 128 |
| C. krusei | NCPF3953 | NP328 | 128 |
| C. krusei | NCPF3953 | NP329 | 32 |
| C. krusei | NCPF3953 | NP337 | 16 |
| C. krusei | NCPF3953 | NP338 | 8 |

TABLE 2-continued

| Genus & Species | Strain | | MIC (μM) |
|---|---|---|---|
| C. krusei | NCPF3953 | NP349 | 8 |
| C. krusei | NCPF3953 | NP350 | 8 |
| C. krusei | NCPF3953 | NP351 | 32 |
| C. krusei | NCPF3953 | NP352 | 32 |
| C. krusei | NCPF3953 | NP354 | >2048 |
| C. krusei | ATCC6258 | NP316 | <16 |
| C. krusei | ATCC6258 | NP317 | <16 |
| C. krusei | ATCC6258 | NP318 | <16 |
| C. krusei | ATCC6258 | NP337 | 2 |
| C. krusei | ATCC6258 | NP338 | 2 |
| C. krusei | ATCC6258 | NP340 | 4 |
| C. parapsilosis | ATCC22019 | NP317 | 256 |
| C. parapsilosis | ATCC22019 | NP318 | 256 |
| C. parapsilosis | ATCC22019 | NP337 | 32 |
| C. parapsilosis | ATCC22019 | NP338 | 8 |
| C. parapsilosis | ATCC22019 | NP340 | 2 |
| C. parapsilosis | ATCC90018 | NP317 | 256 |
| C. parapsilosis | ATCC90018 | NP337 | 128 |
| C. parapsilosis | ATCC90018 | NP338 | 128 |
| C. parapsilosis | ATCC90018 | NP340 | 2 |
| C. tropicalis | ATCC750 | NP337 | 2 |
| C. tropicalis | ATCC750 | NP338 | 2 |
| C. tropicalis | ATCC750 | NP340 | 2 |

| Genus & Species | Strain | MIC (μM) |
|---|---|---|
| NP339 Yeast MIC Data | | |
| C. albicans | ATCC24433 | 2 |
| C. albicans | ATCC90028 | 2 |
| C. albicans | NCTC3179 | 2 |
| C. albicans | 73/034 | 1 |
| C. albicans | AM2003-020 | 2 |
| C. albicans | AM2003-0191 | 1 |
| C. albicans | AM2003-0069 | 2 |
| C. albicans | AM2003-0100 | 2 |
| C. albicans | AM2003-0182 | 2 |
| C. albicans | AM2004-0025 | 1 |
| C. albicans | AM2005-0377 | 2 |
| C. albicans | HUN68 | 2 |
| C. albicans | IHEM3742 | 2 |
| C. albicans | IHEM16614 | 1 |
| C. albicans | IHEM16945 | 4 |
| C. albicans | IHEM16972 | 1 |
| C. albicans | L1086 | 2 |
| C. albicans | RV4688 | 2 |
| C. albicans | s20122.073 | 2 |
| C. albicans | s20152.013 | 2 |
| C. albicans | s20152.082 | 4 |
| C. albicans | s20175.016 | 2 |
| C. albicans | s20176.079 | 8 |
| C. albicans | SC5314 | 2 |
| C. glabrata | AM2002/0085 | 2 |
| C. glabrata | AM2002/0088 | 1 |
| C. glabrata | AM2007/0113 | 2 |
| C. glabrata | AM2007/0114 | 1 |
| C. glabrata | AM2007/0115 | 2 |
| C. glabrata | AM2007/0116 | 1 |
| C. glabrata | AM2007/0117 | 1 |
| C. glabrata | AM2007/0118 | 2 |
| C. glabrata | AM2007/0119 | 1 |
| C. glabrata | AM2007/0120 | 2 |
| C. glabrata | AM2007/0121 | 1 |
| C. glabrata | AM2007/0122 | 1 |
| C. glabrata | AM2007/0123 | 1 |
| C. glabrata | AM2007/0124 | 1 |
| C. glabrata | AM2007/0125 | 2 |
| C. glabrata | AM2007/0126 | 1 |
| C. glabrata | AM2007/0127 | 1 |
| C. glabrata | AM2007/0128 | 1 |
| C. glabrata | AM2007/0129 | 1 |
| C. glabrata | AM2007/0130 | 1 |
| C. krusei | ATCC6258 | 2 |
| C. krusei | AM2007/0102 | 2 |
| C. krusei | AM2007/0103 | 2 |
| C. krusei | AM2007/0104 | 1 |
| C. krusei | AM2007/0105 | 1 |
| C. krusei | AM2007/0106 | 1 |
| C. krusei | AM2007/0107 | 1 |
| C. krusei | AM2007/0109 | 1 |
| C. krusei | AM30274.04 | 2 |
| C. krusei | AM30308.03.05 | 1 |
| C. krusei | AM30332.04.05 | 2 |
| C. krusei | AM30455.04.05 | 1 |
| C. krusei | AM2005/0492 | 1 |
| C. krusei | AM2005/0494 | 1 |
| C. krusei | AM2005/0496 | 2 |
| C. krusei | AM2005/0498 | 1 |
| C. krusei | AM2005/0525 | 2 |
| C. krusei | AM2005/0531 | 2 |
| C. krusei | AM2006/0127 | 1 |
| C. krusei | AM31194/04/05 | 2 |
| C. krusei | AM31300/04/05 | 2 |
| C. parapsilosis | ATCC90018 | 2 |
| C. parapsilosis | ATCC22019 | 1-2 |
| C. parapsilosis | AM2004/0133 | 1-2 |
| C. parapsilosis | AM2005-0112 | 2 |
| C. parapsilosis | AM2005/0233 | 8 |
| C. parapsilosis | AM2005/0237 | 1 |
| C. parapsilosis | AM2005/0238 | 16 |
| C. parapsilosis | AM2005/0239 | 1 |
| C. parapsilosis | AM2005/0242 | 4 |
| C. parapsilosis | AM2005/0337 | 2-16 |
| C. parapsilosis | AM2007/0131 | 4-32 |
| C. parapsilosis | AM2007/0132 | 16-32 |
| C. parapsilosis | AM2007/0134 | 4-32 |
| C. parapsilosis | AM2007/0135 | 1-2 |
| C. parapsilosis | AM2007/0136 | 2 |
| C. parapsilosis | AM2007/0137 | 8-32 |
| C. parapsilosis | AM2007/0138 | 16-32 |
| C. parapsilosis | AM2007/0139 | 8 |
| C. tropicalis | ATCC750 | 2 |
| C. tropicalis | AM2004/0087 | 1 |
| C. tropicalis | AM2004/0088 | 1 |
| C. tropicalis | AM2004/0089 | 1 |
| C. tropicalis | AM2004/0090 | 1 |
| C. tropicalis | AM2004/0091 | 1 |
| Cryptococcus neoformans | DSM11959 | 1 |
| NP341 Yeast MIC Data | | |
| C. albicans | ATCC24433 | 2 |
| C. albicans | ATCC90028 | 1 |
| C. albicans | NCTC3179 | 2 |
| C. albicans | s20176.079 | 32 |
| C. albicans | AM2007/0069 | 2 |
| C. albicans | IHEM3743 | 8 |
| C. albicans | IHEM16945 | 32 |
| C. albicans | SC5314 | 2 |
| C. glabrata | NCPF3943 | 4 |
| C. glabrata | NCPF3831 | 1 |
| C. glabrata | AM2002/0085 | 2 |
| C. glabrata | AM2002/0088 | 1 |
| C. glabrata | AM2007/0113 | 1 |
| C. glabrata | AM2007/0114 | 1 |
| C. glabrata | AM2007/0115 | 1 |
| C. glabrata | AM2007/0116 | 2 |
| C. glabrata | AM2007/0117 | 2 |
| C. glabrata | AM2007/0118 | 2 |
| C. glabrata | AM2007/0119 | 1 |
| C. glabrata | AM2007/0120 | 1 |
| C. glabrata | AM2007/0121 | 1 |
| C. glabrata | AM20070122 | 1 |
| C. glabrata | AM2007/0125 | 1 |
| C. glabrata | AM2007/0126 | 1 |
| C. glabrata | AM2007/0127 | 1 |
| C. glabrata | AM20070128 | 1 |
| C. glabrata | AM2007/0129 | 1 |
| C. glabrata | AM2007/0130 | 2 |
| C. krusei | ATCC6258 | 1 |
| C. krusei | NCPF3953 | 1 |
| C. krusei | AM30308/03/05 | 2 |
| C. krusei | AM2007/0106 | 2 |
| C. krusei | AM2007/0105 | 2 |
| C. krusei | AM30308/03/058 | 2 |
| C. krusei | AM2005/0492 | 1 |
| C. krusei | AM2005/0494 | 1 |
| C. krusei | AM2005/0496 | 1 |
| C. krusei | AM2005/0498 | 2 |
| C. krusei | AM2005/0525 | 2 |

TABLE 2-continued

| | | |
|---|---|---|
| C. krusei | AM2005/0531 | 1 |
| C. krusei | AM2006/0127 | 2 |
| C. krusei | AM31194/04/05 | 1 |
| C. krusei | AM31300/04/05 | 2 |
| C. parapsilosis | ATCC90018 | 2 |
| C. parapsilosis | ATCC22019 | 1 |
| C. parapsilosis | AM2005/0358 | 4 |
| C. parapsilosis | AM2005/0225 | 4-32 |
| C. parapsilosis | AM2007/0135 | 2 |
| C. parapsilosis | AM2007/0137 | 8 |
| C. parapsilosis | AM2005-0112 | 2 |
| C. tropicalis | ATCC750 | 1 |
| C. tropicalis | AM2005/0087 | 1 |
| C. tropicalis | AM2004/0088 | 1 |
| C. tropicalis | AM2005/0089 | 1 |
| C. tropicalis | AM2005/00110 | 1 |
| C. tropicalis | AM2005/00111 | 2 |
| Cryptococcus neoformans | DSM11959 | 1 |

NP339 Aspergillus spp. MIC Data

| | | |
|---|---|---|
| A nidulans | NCPF2691 | 3.9 |
| A nidulans | AFG97-71 | 4000 |
| A. nidulans | AFG97-453 | 62.5 |
| A. nidulans | AFG 98-281 | 62.5 |
| A. nidulans | AFG9811-35 | 125 |
| A nidulans | AFG99-247 | 256 |
| A nidulans | AFG99-1373 | 62.5 |
| A. nidulans | AFG99-2387 | 62.5 |
| A. nidulans | AFG00-676 | 1000 |
| A. nidulans | AFG01-835 | 1000 |
| A. nidulans | AFG01-1716 | 62.5 |
| A. nidulans | AFGR2952 | 62.5 |
| A. niger | NCPF2022 | 7.8 |
| A. niger | AFG 01-2620 | >4000 |
| A. niger | AFG 01-2840 | 62.5 |
| A. niger | AFG 01-783 | 62.5 |
| A. niger | AFG 01-237 | 1000 |
| A. niger | AFG 01-385 | 1000 |
| A. niger | AFG 01-1494 | 62.5 |
| A. niger | AFG 01-2103 | 62.5 |
| A. niger | AFG 01-60 | 62.5 |
| A. niger | AFG 01-1286 | 62.5 |
| A. niger | AFG 01-423 | 62.5 |
| A. niger | AFG 01-1237 | 62.5 |
| A. niger | AFG 01-2267 | 62.5 |
| A. niger | AFG 01-381 | 62.5 |
| A. niger | AFG 01-2112 | 62.5 |
| A. niger | AFG 01-809 | 62.5 |
| A. niger | AFG 01-1424 | 62.5 |
| A. niger | AFG J970467 | 62.5 |
| A. niger | AFG J940179 | 62.5 |

NP341 Aspergillus spp. MIC Data

| | | |
|---|---|---|
| A nidulans | AFG97-71 | 4000 |
| A. nidulans | AFG99-242 | 62.5 |
| A. nidulans | AFG01-1716 | 62.5 |
| A. nidulans | AFG00676 | 512 |
| A. nidulans | AGFR2952 | 62.5 |
| A. nidulans | AFG01-835 | 512 |
| A. nidulans | AFG97-453 | 62.5 |
| A. nidulans | AFG99-1373 | >4000 |
| A. nidulans | AFG99-2387 | 256 |
| A. nidulans | AFG9811-35 | 2048 |
| A. nidulans | AFG 01-835 | 1024 |
| A. nidulans | AFG 01-1716 | 62.5 |
| A. nidulans | AFG 99-2387 | 62.5 |
| A. nidulans | AFG 98-281 | 62.5 |
| A. niger | AFG 01-2620 | >4000 |
| A. niger | AFG 01-2840 | 62.5 |
| A. niger | AFG 01-783 | 62.5 |
| A. niger | AFG 01-237 | 62.5 |
| A. niger | AFG 01-385 | 62.5 |
| A. niger | AFG 01-1494 | 62.5 |
| A. niger | AFG 01-2103 | 62.5 |
| A. niger | AFG 01-60 | 62.5 |
| A. niger | AFG 01-1286 | 62.5 |
| A. niger | AFG 01-423 | 62.5 |
| A. niger | AFG 01-1237 | 62.5 |
| A. niger | AFG 01-2267 | 62.5 |
| A. niger | AFG 01-381 | 62.5 |
| A. niger | AFG 01-2112 | 62.5 |
| A. niger | AFG 01-809 | 62.5 |
| A. niger | AFG 01-1424 | 62.5 |
| A. niger | AFG J970467 | 62.5 |
| A. niger | AFG J940179 | 62.5 |

Other Fungi and Yeasts MIC Data

| Genus & Species | Strain | Peptide | MIC (µM) |
|---|---|---|---|
| Alternaria spp. | DM 2006 1218a | NP108 | 62.5 (µg/ml) |
| Alternaria spp. | DM 2006 1218a | NP121 | 13.2 (µg/ml) |
| Alternaria spp. | DM 2006 1218a | NP339 | 7.8 |
| Fusarium solani | NCPF2877 | NP108 | 256 (µg/ml) |
| Fusarium solani | NCPF2877 | NP121 | 7.8 (µg/ml) |
| Fusarium solani | NCPF2877 | NP339 | 3.9 |
| Fusarium spp. | DM 2006 1133 | NP108 | 125 (µg/ml) |
| Fusarium spp. | DM 2006 1133 | NP121 | 156 (µg/ml) |
| Fusarium spp. | DM 2006 1133 | NP339 | 125 |
| Malasezzia furfur | DSM6170 | NP316 | 125 |
| Malasezzia furfur | DSM6170 | NP317 | <15.6 |
| Malasezzia furfur | DSM6170 | NP318 | 62.5 |
| Malasezzia furfur | DSM6170 | NP319 | 256 |
| Malasezzia furfur | DSM6170 | NP337 | 31.25 |
| Malasezzia furfur | DSM6170 | NP338 | <15.6 |
| Malasezzia furfur | DSM6170 | NP112 | 512 (µg/ml) |
| Penicillium spp. | DM 2006 1285b | NP108 | 31.2 (µg/ml) |
| Penicillium spp. | DM 2006 1285b | NP121 | 15.6 (µg/ml) |
| Penicillium spp. | DM 2006 1285b | NP339 | 15.6 |
| Scopulariopsis brevicaulis | DM 2006 1025 | NP108 | 3.9 (µg/ml) |
| Scopulariopsis brevicaulis | DM 2006 1025 | NP121 | 3.9 (µg/ml) |
| Scopulariopsis brevicaulis | DM 2006 1025 | NP339 | 1 |
| Trichophyton rubrum | NCPF118 | NP301 | >2 |
| Trichophyton rubrum | NCPF118 | NP302 | >2 |
| Trichophyton rubrum | NCPF118 | NP303 | >2 |
| Trichophyton rubrum | NCPF118 | NP304 | >2 |
| Trichophyton rubrum | NCPF118 | NP305 | >2 |
| Trichophyton rubrum | NCPF118 | NP306 | >2 |
| Trichophyton rubrum | NCPF118 | NP307 | >2 |
| Trichophyton rubrum | NCPF118 | NP308 | >2 |
| Trichophyton rubrum | NCPF118 | NP309 | >2 |
| Trichophyton rubrum | NCPF118 | NP310 | >2 |
| Trichophyton rubrum | NCPF118 | NP316 | 0.5 |
| Trichophyton rubrum | NCPF118 | NP317 | 0.25 |
| Trichophyton rubrum | NCPF118 | NP318 | >2 |
| Trichophyton rubrum | NCPF118 | NP319 | >2 |

Candida spp. Type Strains MIC Data table (µM)

| Peptide | Candida albicans NCTC3179 | Candida albicans ATCC24433 | Candida albicans ATCC90028 | Candida krusei NCPF3953 |
|---|---|---|---|---|
| NP301 | >2000 | ND | ND | ND |
| NP302 | >2000 | ND | ND | ND |
| NP303 | >2000 | ND | ND | ND |
| NP304 | >2000 | ND | ND | ND |
| NP305 | >2000 | ND | ND | ND |
| NP306 | >2000 | ND | ND | ND |
| NP307 | >2000 | ND | ND | ND |
| NP308 | >2000 | ND | ND | ND |
| NP309 | >2000 | ND | ND | ND |
| NP310 | >2000 | ND | ND | ND |
| NP311 | >2000 | ND | ND | ND |
| NP316 | >2000 | ND | ND | 8 |
| NP317 | 512 | ND | ND | 32 |
| NP318 | 4 | ND | ND | 8 |
| NP319 | 4 | ND | ND | 8 |
| NP320 | >2000 | ND | ND | ND |
| NP321 | >2000 | ND | ND | ND |
| NP322 | >2000 | ND | ND | ND |
| NP323 | 1024 | 1024 | 2000 | 256 |
| NP324 | 1024 | 1024 | 1024 | 256 |
| NP325 | >2000 | ND | ND | ND |
| NP326 | 2000 | 1024 | 1024 | 128 |
| NP327 | 512 | 1024 | 512 | 64 |
| NP328 | 1024 | 1024 | 1024 | 128 |
| NP329 | 256 | 512 | ND | 32 |
| NP331 | >2000 | ND | ND | ND |

TABLE 2-continued

| | | | | |
|---|---|---|---|---|
| NP332 | >2000 | ND | ND | ND |
| NP333 | >2000 | ND | ND | ND |
| NP334 | >2000 | ND | ND | ND |
| NP335 | >2000 | ND | ND | ND |
| NP336 | >2000 | ND | ND | ND |
| NP337 | 2 | 2 | 4 | 16 |
| NP338 | 2 | 2 | 4 | 8 |

TABLE 2-continued

| | | | | |
|---|---|---|---|---|
| NP339 | ND | ND | 2 | ND |
| NP340 | ND | ND | 2 | ND |

Certain *Aspergillus* spp strains including *Aspergillus terreus*, *Aspergillus fumigatus* and *Aspergillus flavus* were found to be insensitive to those peptides tested (data not shown).

The invention claimed is:

1. A method for the treatment or alleviation of a fungal infection in a subject, comprising administering to the subject a peptide or pharmaceutically acceptable salt thereof, wherein the peptide is selected from the group consisting of:
   (a) a peptide consisting of a sequence of 11 to 15 contiguous arginine residues; and
   (b) a peptide consisting of a sequence having 1 or 2 amino acid substitutions to the sequence recited in (a).

2. The method of claim 1 wherein the fungal infection is a dermatophyte infection.

3. The method of claim 1 wherein the fungal infection is a non-dermatophyte infection.

4. The method of claim 3 wherein the non-dermatophyte infection is caused by a fungus selected from the group consisting of *Absidia* species, *Aspergillus* species, *Cryptococcus* species, *Malassezia* species, *Candida* species, *Rhizomucor* species, *Saccharomyces* species, *Hansenula* species, *Fusarium* species, *Mucor* species, *Trichosporon* species, *Rhodotorula* species, *Pichia* species, *Rhizopus* species, *Penicillium* species, and *Blastoschizomyces* species.

5. The method of claim 4, wherein the fungus is selected from the group consisting of: *Aspergillus* species, *Fusarium* species, *Candida* species, *Alternaria* species, *Penicillium* species, *Scopulariopsis* species, *Malassezia* species, and *Cryptococcus* species.

6. The method of claim 5 wherein the fungus is *Candida* species.

7. The method of claim 1 wherein the fungal infection is a systemic mycosis.

8. The method of claim 7 wherein the systemic mycosis is selected from the group consisting of: histoplasmosis, coccidioidomycosis, blastomycosis, paracoccidioidomycosis, aspergillosis, candidiasis, fusariosis, cryptococcosis, phaeohyphomycosis, hyalohyphomycosis, fungemia, mucormycosis, alternariosis, trichosporonosis and chromomycosis.

9. The method of claim 7 wherein the systemic mycosis is an opportunistic mycosis selected from the group consisting of: aspergillosis, alternariosis, candidiasis, fusariosis, and cryptococcosis.

10. The method of claim 1 wherein the fungal infection is selected from the group consisting of: pneumonia, oropharyngeal candidiasis, esophageal candidiasis, pulmonary aspergillosis, cerebral infection, rhinosinusitis, pulmonary cryptococcosis, meningitis, rhinocerebral mucormycosis and pulmonary mucormycosis.

11. The method of claim 1, wherein the fungal infection is a nosocomial disorder.

12. The method of claim 1 wherein the peptide or pharmaceutically acceptable salt thereof, is formulated for inhalation.

13. The method of claim 1 wherein the peptide or pharmaceutically acceptable salt thereof, is formulated for parental administration.

14. A method for the treatment of a fungal infection in a subject, comprising administering to the subject a peptide or pharmaceutically acceptable salt thereof, wherein the peptide consists of 11 to 15 contiguous arginine residues.

15. The method of claim 14, wherein the fungal infection is caused by a fungus selected from the group consisting of: *Aspergillus* species, *Fusarium* species, *Candida* species, *Alternaria* species, *Penicillium* species, *Scopulariopsis* species, *Malassezia* species, and *Cryptococcus* species.

16. The method of claim 14, wherein the fungal infection is caused by a fungus selected from the group consisting of: *Aspergillus nidulans, Aspergillus niger, Candida glabrata, Candida tropicalis, Candida parapsilosis, Candida tropicales, Candida albicans, Candida krusei, Cryptococcus neoformans, Fusarium solani, Malassezia furfur*, and *Scopulariopsis brevicaulis*.

17. The method of claim 1, wherein the peptide is linear.

18. The method of claim 1, wherein the peptide consists of D-amino acids.

19. The method of claim 14, wherein the peptide is linear.
20. The method of claim 14, wherein the peptide consists of D-amino acids.

* * * * *